US007789879B2

(12) United States Patent
Palanker et al.

(10) Patent No.: US 7,789,879 B2
(45) Date of Patent: Sep. 7, 2010

(54) SYSTEM FOR PLASMA-MEDIATED THERMO-ELECTRICAL SURGERY

(75) Inventors: Daniel V. Palanker, Sunnyvale, CA (US); Alexander B. Vankov, Menlo Park, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 24 days.

(21) Appl. No.: 11/726,782

(22) Filed: Mar. 22, 2007

(65) Prior Publication Data

US 2007/0239156 A1  Oct. 11, 2007

Related U.S. Application Data

(63) Continuation of application No. 10/825,716, filed on Apr. 16, 2004, now Pat. No. 7,238,185, which is a continuation of application No. 10/137,814, filed on May 3, 2002, now Pat. No. 6,780,178.

(51) Int. Cl.
    A61B 18/18 (2006.01)
(52) U.S. Cl. .............................. 606/42; 606/38; 606/41; 606/34; 606/45
(58) Field of Classification Search ................. 606/34, 606/37, 38–42, 45–50
    See application file for complete search history.

(56) References Cited

U.S. PATENT DOCUMENTS 3,799,168 A    3/1974  Peters (Continued)

FOREIGN PATENT DOCUMENTS

EP    0 012 037 A1    6/1980

(Continued)

OTHER PUBLICATIONS

Jones, H.M. et al. (Jan. 15, 1995). "Pulsed Dielectric Breakdown of Pressurized Water and Salt Solutions," *J. Appl. Phys.* 77(2):795-805.

(Continued)

*Primary Examiner*—Linda C Dvorak
*Assistant Examiner*—Amanda Scott
(74) *Attorney, Agent, or Firm*—Morrison & Foerster LLP (57) ABSTRACT

An apparatus and method for cutting a material including conducting and non-conducting materials such as biological tissue, cellulose or plastic while the material is submerged in a conductive liquid medium. The apparatus has a cutting electrode with an elongate cutting portion having an aspect ratio (length to width) of 1 or more and a return electrode. The two electrodes are immersed in the conductive medium and a voltage is applied between them to heat the medium, thus producing a vapor cavity around the elongate cutting portion and ionizing a gas inside the vapor cavity to produce a plasma. The voltage applied between the electrodes is modulated in pulses having a modulation format selected to minimize the size of the vapor cavity, its rate of formation and heat diffusion into the material while the latter is cut with an edge of the elongate cutting portion. The modulation format includes pulses ranging in duration from 10 μs to 10 ms, as well as minipulses and micropulses, as necessary. The apparatus and method of invention allow the user to perform efficient thermal ablation and electrosurgical procedures in particular at power levels as low as 10 mW with minimal thermal and cavitation damage.

19 Claims, 8 Drawing Sheets

U.S. PATENT DOCUMENTS

| | | | |
|---|---|---|---|
| 3,903,891 A | 9/1975 | Brayshaw | |
| 3,970,088 A | 7/1976 | Morrison | |
| 3,987,795 A | 10/1976 | Morrison | |
| 4,034,762 A * | 7/1977 | Cosens et al. | 606/40 |
| 4,043,342 A | 8/1977 | Morrison, Jr. | |
| 4,074,718 A | 2/1978 | Morrison, Jr. | |
| 4,161,950 A | 7/1979 | Doss et al. | |
| 4,202,337 A | 5/1980 | Hren et al. | |
| 4,228,800 A | 10/1980 | Degler, Jr. et al. | |
| 4,248,231 A | 2/1981 | Herczog et al. | |
| 4,429,694 A | 2/1984 | McGreevy | |
| 4,476,862 A | 10/1984 | Pao | |
| 4,492,231 A | 1/1985 | Auth | |
| 4,534,347 A | 8/1985 | Taylor | |
| 4,559,943 A | 12/1985 | Bowers | |
| 4,589,411 A | 5/1986 | Friedman | |
| 4,590,934 A | 5/1986 | Malis et al. | |
| 4,593,691 A | 6/1986 | Lindstrom et al. | |
| 4,597,388 A | 7/1986 | Koziol et al. | |
| 4,655,215 A | 4/1987 | Pike | |
| 4,674,499 A | 6/1987 | Pao | |
| 4,781,175 A | 11/1988 | McGreevy et al. | |
| 4,805,616 A | 2/1989 | Pao | |
| 4,901,709 A | 2/1990 | Rattner et al. | |
| 4,927,420 A | 5/1990 | Newkirk et al. | |
| 4,936,301 A | 6/1990 | Rexroth et al. | |
| 4,938,761 A | 7/1990 | Ensslln | |
| 4,943,290 A | 7/1990 | Rexroth et al. | |
| 5,080,660 A | 1/1992 | Buelna | |
| 5,088,997 A | 2/1992 | Delahuerga et al. | |
| 5,108,391 A | 4/1992 | Flachenecker et al. | |
| 5,217,457 A | 6/1993 | Delahuerga et al. | |
| 5,254,121 A | 10/1993 | Manevitz et al. | |
| 5,267,994 A | 12/1993 | Gentelia et al. | |
| 5,281,216 A | 1/1994 | Klicek | |
| 5,300,068 A * | 4/1994 | Rosar et al. | 606/34 |
| 5,318,563 A | 6/1994 | Malis et al. | |
| 5,348,553 A | 9/1994 | Whitney | |
| 5,423,814 A | 6/1995 | Zhu et al. | |
| 5,454,809 A | 10/1995 | Janssen | |
| 5,496,314 A | 3/1996 | Eggers | |
| 5,549,604 A | 8/1996 | Sutcu et al. | |
| 5,569,242 A | 10/1996 | Lax et al. | |
| 5,599,346 A | 2/1997 | Edwards et al. | |
| 5,647,871 A | 7/1997 | Levine et al. | |
| 5,658,279 A | 8/1997 | Nardella et al. | |
| 5,669,904 A * | 9/1997 | Platt et al. | 606/27 |
| 5,683,366 A | 11/1997 | Eggers et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,700,262 A | 12/1997 | Acosta et al. | |
| 5,766,153 A | 6/1998 | Eggers et al. | |
| 5,766,170 A | 6/1998 | Eggers | |
| 5,785,704 A | 7/1998 | Bille et al. | |
| 5,843,019 A | 12/1998 | Eggers et al. | |
| 5,860,976 A | 1/1999 | Billings et al. | |
| 5,873,855 A | 2/1999 | Eggers et al. | |
| 5,891,095 A | 4/1999 | Eggers et al. | |
| 5,891,142 A | 4/1999 | Eggers et al. | |
| 5,958,266 A | 9/1999 | Fugo et al. | |
| 6,004,319 A | 12/1999 | Goble et al. | |
| 6,032,674 A | 3/2000 | Eggers et al. | |
| 6,047,700 A | 4/2000 | Eggers et al. | |
| 6,053,172 A | 4/2000 | Hovda et al. | |
| 6,056,746 A | 5/2000 | Goble et al. | |
| 6,059,782 A | 5/2000 | Novak | |
| 6,059,783 A | 5/2000 | Kirwan, Jr. | |
| 6,066,134 A | 5/2000 | Eggers et al. | |
| 6,066,137 A | 5/2000 | Greep | |
| 6,102,046 A | 8/2000 | Weinstein et al. | |
| 6,113,594 A | 9/2000 | Savage | |
| 6,132,427 A | 10/2000 | Jones et al. | |
| 6,135,998 A | 10/2000 | Palanker | |
| 6,149,620 A | 11/2000 | Baker et al. | |
| 6,149,646 A | 11/2000 | West, Jr. et al. | |
| 6,165,175 A | 12/2000 | Wampler et al. | |
| 6,174,309 B1 | 1/2001 | Wrublewski et al. | |
| 6,183,469 B1 | 2/2001 | Thapliyal et al. | |
| 6,190,381 B1 | 2/2001 | Olsen et al. | |
| 6,210,404 B1 | 4/2001 | Shadduck | |
| 6,228,081 B1 * | 5/2001 | Goble | 606/34 |
| 6,228,082 B1 | 5/2001 | Baker et al. | |
| 6,228,084 B1 | 5/2001 | Kirwan, Jr. | |
| 6,254,600 B1 | 7/2001 | Willink et al. | |
| 6,267,757 B1 | 7/2001 | Aita et al. | |
| 6,287,305 B1 | 9/2001 | Heim et al. | |
| 6,287,306 B1 | 9/2001 | Kroll et al. | |
| 6,352,535 B1 | 3/2002 | Lewis et al. | |
| 6,355,032 B1 | 3/2002 | Hovda et al. | |
| 6,358,248 B1 | 3/2002 | Mulier et al. | |
| 6,364,877 B1 | 4/2002 | Goble et al. | |
| 6,398,779 B1 | 6/2002 | Buysse et al. | |
| 6,447,511 B1 | 9/2002 | Slater | |
| 6,458,121 B1 | 10/2002 | Rosenstock et al. | |
| 6,478,794 B1 | 11/2002 | Trapp et al. | |
| 6,479,785 B1 | 11/2002 | Fugo et al. | |
| 6,482,201 B1 | 11/2002 | Olsen et al. | |
| 6,482,205 B1 | 11/2002 | Bonnet | |
| 6,500,176 B1 | 12/2002 | Truckai et al. | |
| 6,530,924 B1 | 3/2003 | Ellman et al. | |
| 6,533,781 B2 | 3/2003 | Heim et al. | |
| 6,544,261 B2 * | 4/2003 | Ellsberry et al. | 606/41 |
| 6,589,237 B2 | 7/2003 | Woloszko et al. | |
| 6,620,160 B2 | 9/2003 | Lewis et al. | |
| 6,679,269 B2 | 1/2004 | Swanson | |
| 6,726,683 B1 | 4/2004 | Shaw | |
| 6,749,608 B2 | 6/2004 | Garito et al. | |
| 6,770,071 B2 | 8/2004 | Woloszko et al. | |
| 6,780,178 B2 | 8/2004 | Palanker et al. | |
| 6,787,730 B2 * | 9/2004 | Coccio et al. | 219/121.44 |
| 6,802,842 B2 | 10/2004 | Ellman et al. | |
| 6,818,102 B1 | 11/2004 | Viol | |
| 6,837,887 B2 | 1/2005 | Woloszko et al. | |
| 6,949,096 B2 | 9/2005 | Davison et al. | |
| 6,960,204 B2 | 11/2005 | Eggers et al. | |
| 6,991,631 B2 | 1/2006 | Woloszko et al. | |
| 7,004,941 B2 | 2/2006 | Tvinnereim et al. | |
| 7,090,672 B2 | 8/2006 | Underwood et al. | |
| 7,094,215 B2 | 8/2006 | Davison et al. | |
| RE39,358 E | 10/2006 | Goble | |
| 7,115,139 B2 | 10/2006 | McClurken et al. | |
| 7,131,969 B1 | 11/2006 | Hovda et al. | |
| 7,169,143 B2 | 1/2007 | Eggers et al. | |
| 7,179,255 B2 | 2/2007 | Lettice et al. | |
| 7,182,762 B2 | 2/2007 | Bortkiewicz | |
| 7,186,234 B2 | 3/2007 | Dahla et al. | |
| 7,192,428 B2 | 3/2007 | Eggers et al. | |
| 7,195,627 B2 | 3/2007 | Amoah et al. | |
| 7,195,630 B2 | 3/2007 | Ciarrocca | |
| 7,201,750 B1 | 4/2007 | Eggers et al. | |
| 7,238,185 B2 | 7/2007 | Palanker et al. | |
| 7,270,658 B2 | 9/2007 | Woloszko et al. | |
| 7,270,661 B2 | 9/2007 | Dahla et al. | |
| 7,276,063 B2 | 10/2007 | Davison et al. | |
| 7,429,262 B2 | 9/2008 | Woloszko et al. | |
| 7,435,247 B2 | 10/2008 | Woloszko et al. | |
| 7,445,618 B2 | 11/2008 | Eggers et al. | |
| 7,468,059 B2 | 12/2008 | Eggers et al. | |
| 2001/0012934 A1 * | 8/2001 | Chandrasekaran et al. | 606/41 |
| 2001/0034519 A1 * | 10/2001 | Goble et al. | 606/41 |
| 2002/0052600 A1 * | 5/2002 | Davison et al. | 606/41 |
| 2004/0162554 A1 | 8/2004 | Lee et al. | |

| | | | | | | |
|---|---|---|---|---|---|---|
| 2004/0199157 | A1 | 10/2004 | Palanker et al. | EP | 1 055 399 A1 | 11/2000 |
| 2004/0236321 | A1 | 11/2004 | Palanker et al. | EP | 1 061 857 B1 | 12/2000 |
| 2004/0267254 | A1 | 12/2004 | Manzo et al. | EP | 1 065 981 B1 | 1/2001 |
| 2005/0021028 | A1 | 1/2005 | Palanker et al. | EP | 1 079 746 B1 | 3/2001 |
| 2005/0220674 | A1 | 10/2005 | Shafirstein et al. | EP | 1 080 680 A1 | 3/2001 |
| 2005/0234439 | A1 | 10/2005 | Underwood | EP | 1 080 694 A1 | 3/2001 |
| 2005/0234446 | A1 | 10/2005 | Van Wyk et al. | EP | 1 082 944 B1 | 3/2001 |
| 2005/0288665 | A1 | 12/2005 | Woloszko | EP | 1 158 917 B1 | 12/2001 |
| 2006/0069386 | A1 | 3/2006 | Dubnack et al. | EP | 1 174 093 B1 | 1/2002 |
| 2006/0155270 | A1 | 7/2006 | Hancock et al. | EP | 1 179 320 A2 | 2/2002 |
| 2006/0253117 | A1 | 11/2006 | Hovda et al. | EP | 1 179 320 A3 | 2/2002 |
| 2006/0259025 | A1 | 11/2006 | Dahla | EP | 1 205 155 A1 | 5/2002 |
| 2006/0259033 | A1 | 11/2006 | Nesbitt | EP | 1 253 866 B1 | 11/2002 |
| 2007/0112348 | A1 | 5/2007 | Eggers et al. | EP | 1 257 220 B1 | 11/2002 |
| 2007/0129715 | A1 | 6/2007 | Eggers et al. | EP | 1 287 788 A1 | 3/2003 |
| 2007/0149966 | A1 | 6/2007 | Dahla et al. | EP | 1 330 201 B1 | 7/2003 |
| 2007/0179497 | A1 | 8/2007 | Eggers et al. | EP | 1 330 989 B1 | 7/2003 |
| 2008/0004621 | A1 | 1/2008 | Dahla et al. | EP | 1 344 498 B1 | 9/2003 |
| 2008/0015565 | A1 | 1/2008 | Davison | EP | 1 374 788 A1 | 1/2004 |
| 2008/0021447 | A1 | 1/2008 | Davison | EP | 1 407 719 A3 | 4/2004 |
| 2008/0027428 | A1 | 1/2008 | Palanker et al. | EP | 1 581 128 B1 | 10/2005 |
| 2008/0039832 | A1 | 2/2008 | Palanker et al. | EP | 1 599 146 B1 | 11/2005 |
| 2008/0119842 | A1 | 5/2008 | Palanker et al. | EP | 1 632 191 A3 | 3/2006 |
| 2008/0125774 | A1 | 5/2008 | Palanker et al. | EP | 1 637 087 A3 | 3/2006 |
| | | | | EP | 1 693 015 A2 | 8/2006 |
| | | FOREIGN PATENT DOCUMENTS | | EP | 1 782 741 A3 | 5/2007 |
| EP | 0 672 841 A2 | 9/1995 | | EP | 1 880 686 A2 | 1/2008 |
| EP | 0 672 841 A3 | 9/1995 | | WO | WO-96/39914 A1 | 12/1996 |
| EP | 0 672 841 B1 | 9/1995 | | WO | WO-97/27893 A1 | 8/1997 |
| EP | 0 694 290 B1 | 1/1996 | | WO | WO-98/03117 A1 | 1/1998 |
| EP | 0 697 841 B1 | 2/1996 | | WO | WO-98/03220 A1 | 1/1998 |
| EP | 0 697 841 B2 | 2/1996 | | WO | WO-99/03407 A1 | 1/1998 |
| EP | 0 708 618 B1 | 5/1996 | | WO | WO-98/56324 A1 | 12/1998 |
| EP | 0 754 437 A3 | 3/1997 | | WO | WO-99/03408 A1 | 1/1999 |
| EP | 0 754 437 B1 | 3/1997 | | WO | WO-99/03409 A1 | 1/1999 |
| EP | 0 754 437 B2 | 3/1997 | | WO | WO-99/09919 A1 | 3/1999 |
| EP | 0 771 176 B1 | 5/1997 | | WO | WO-99/16359 A1 | 4/1999 |
| EP | 0 771 176 B2 | 5/1997 | | WO | WO-99/20213 A1 | 4/1999 |
| EP | 0 820 249 B1 | 1/1998 | | WO | WO-99/30655 A1 | 6/1999 |
| EP | 0 833 593 B1 | 4/1998 | | WO | WO-99/32042 A1 | 7/1999 |
| EP | 0 833 593 B2 | 4/1998 | | WO | WO-99/40858 A1 | 8/1999 |
| EP | 0 837 647 B1 | 4/1998 | | WO | WO-99/49799 A1 | 10/1999 |
| EP | 0 858 295 B1 | 8/1998 | | WO | WO-00/09053 A1 | 2/2000 |
| EP | 0 865 256 B1 | 9/1998 | | WO | WO-00/41638 A1 | 7/2000 |
| EP | 0 869 742 B1 | 10/1998 | | WO | WO-00/54683 A1 | 9/2000 |
| EP | 0 873 089 B1 | 10/1998 | | WO | WO-00/62685 A1 | 10/2000 |
| EP | 0 882 430 A2 | 12/1998 | | WO | WO-00/62698 A1 | 10/2000 |
| EP | 0 882 430 B1 | 12/1998 | | WO | WO-00/71043 A1 | 11/2000 |
| EP | 0 886 493 B1 | 12/1998 | | WO | WO-01/35845 A1 | 5/2001 |
| EP | 0 887 046 B1 | 12/1998 | | WO | WO-01/60273 A1 | 8/2001 |
| EP | 0 923 907 A1 | 6/1999 | | WO | WO-01/95819 A1 | 12/2001 |
| EP | 0 949 886 B1 | 10/1999 | | WO | WO-02/11635 A1 | 2/2002 |
| EP | 0 959 784 B1 | 12/1999 | | WO | WO-02/19932 A1 | 3/2002 |
| EP | 0 959 786 B1 | 12/1999 | | WO | WO 03/092521 A1 | 11/2002 |
| EP | 0 959 787 B1 | 12/1999 | | WO | WO-02/102255 A1 | 12/2002 |
| EP | 0 996 378 B1 | 5/2000 | | WO | WO-03/005882 A2 | 1/2003 |
| EP | 1 018 994 B1 | 7/2000 | | WO | WO-03/005882 A3 | 1/2003 |
| EP | 1 025 807 A3 | 8/2000 | | WO | WO-03/024305 A2 | 3/2003 |
| EP | 1 025 807 B1 | 8/2000 | | WO | WO-03/024305 A3 | 3/2003 |
| EP | 1 026 996 B1 | 8/2000 | | WO | WO-03/024339 A1 | 3/2003 |
| EP | 1 027 020 B1 | 8/2000 | | WO | WO-03/028542 A2 | 4/2003 |
| EP | 1 034 746 A3 | 9/2000 | | WO | WO-03/028542 A3 | 4/2003 |
| EP | 1 034 746 B1 | 9/2000 | | WO | WO-03/068311 A2 | 8/2003 |
| EP | 1 034 747 A1 | 9/2000 | | WO | WO-03/068311 A3 | 8/2003 |
| EP | 1 034 748 A1 | 9/2000 | | WO | WO-03/090638 A1 | 11/2003 |
| EP | 1 036 547 A2 | 9/2000 | | WO | WO-2004/002293 A2 | 1/2004 |
| EP | 1 036 547 A3 | 9/2000 | | WO | WO-2004/002293 A3 | 1/2004 |
| EP | 1 039 862 B1 | 10/2000 | | WO | WO-2004/022155 A2 | 3/2004 |
| EP | 1 041 933 B1 | 10/2000 | | WO | WO-2004/022155 A3 | 3/2004 |
| EP | 1 050 278 A1 | 11/2000 | | WO | WO-2004/071278 A2 | 8/2004 |
| EP | 1 053 719 A1 | 11/2000 | | WO | WO-2004/071278 A3 | 8/2004 |
| EP | 1 053 720 A1 | 11/2000 | | WO | WO-2004/073752 A2 | 9/2004 |
| | | | | WO | WO-2004/073752 A3 | 9/2004 |

| WO | WO-2004/112581 A2 | 12/2004 |
| WO | WO-2004/112581 A3 | 12/2004 |
| WO | WO-2005/009213 A2 | 2/2005 |
| WO | WO-2005/009213 A3 | 2/2005 |
| WO | WO-2005/072634 A2 | 8/2005 |
| WO | WO-2005/072634 A3 | 8/2005 |
| WO | WO-2005/112806 A2 | 12/2005 |
| WO | WO-2005/112806 A3 | 12/2005 |
| WO | WO-2005/117735 A1 | 12/2005 |
| WO | WO-2005/122936 A1 | 12/2005 |
| WO | WO-2005/122938 A1 | 12/2005 |
| WO | WO-2006/002337 A2 | 1/2006 |
| WO | WO-2006/002337 A3 | 1/2006 |
| WO | WO-2006/051252 A1 | 5/2006 |
| WO | WO-2006/125007 A2 | 11/2006 |
| WO | WO-2006/125007 A3 | 11/2006 |
| WO | WO-2007/103800 A2 | 9/2007 |
| WO | WO-2007/103800 A3 | 9/2007 |
| WO | WO-2007/143445 A2 | 12/2007 |
| WO | WO-2007/143445 A3 | 12/2007 |

OTHER PUBLICATIONS

Jones, H.M. et al. (1995). "Development of Pulsed Dielectric Breakdown in Liquids," *J. Phys. D: Appl. Phys.* 28:178-188.

Palanker, D. et al. (2002). "Effect of the Probe Geometry on Dynamics of Cavitation," *Proc. SPIE* 4617:112-117.

Palanker, D. et al. (Jun. 1, 1997). "Electrical Alternative to Pulsed Fiber-delivered Lasers in Microsurgery," *J. Appl. Phys.* 81(11):7673-7680.

Partial European Search Report mailed on Jul. 3, 2008, for EP Application No. 04 71 1134, filed on Sep. 14, 2005, five pages.

European Examination Report mailed on Dec. 12, 2008, for EP Application No. 04755740.0 filed on Jun. 18, 2004, four pages.

European Search Report mailed on Jul. 18, 2007, for EP Application No. 04755740.0 filed on Jun. 18, 2004, four pages.

International Search Report and Written Opinion mailed on May 15, 2008, for PCT Application PCT/US2007/023130, filed on Nov. 1, 2007, eight pages.

International Search Report mailed on Dec. 8, 2005, for PCT Application No. PCT/US04/19785, filed on Jun. 18, 2004, one page.

Cushing, H. (Dec. 1928). "Electro-Surgery as an aid to the Removal of Intracranial Tumors,"vol. XLVII, No. 6 in *Surgery, Gynecology and Obstetrics*, Martin, F. ed. et al., Chicago, Illinois, U.S.A., pp. 751-784.

International Preliminary Report on Patentability mailed on May 14, 2009, for PCT Application No. PCT/US2007/023130, filed on Nov. 1, 2007, seven pages.

Mylrea, K.C. et al. (Jul.-Sep. 1981). "Introduction to Electrosurgery," *Journal of Clinical Engineering* 6(3):185-191.

International Preliminary Report on Patentability mailed on Oct. 15, 2009, for PCT Application No. PCT/US2008/004460, filed on Apr. 4, 2008, six pages.

* cited by examiner

SYSTEM FOR PLASMA-MEDIATED THERMO-ELECTRICAL SURGERY

CROSS REFERENCE TO RELATED APPLICATIONS

This application is a continuation of U.S. patent application Ser. No. 10/825,716 filed Apr. 16, 2004, now known as U.S. Pat. No. 7,238,185, which is a continuation of U.S. patent application Ser. No. 10/137,814 filed May 3, 2002, now known as U.S. Pat. No. 6,780,178, the contents of which are hereby incorporated by reference in their entirety.

GOVERNMENT SPONSORSHIP

This invention was supported by the National Institutes of Health under contract number RO1 EY 12888-02. The government has certain rights in this invention.

FIELD OF THE INVENTION

The present invention relates to an apparatus for cutting materials including biological tissue by thermo-electrical ablation with the aid of a plasma produced around a cutting electrode and to a method for driving such electrode with appropriate pulses.

BACKGROUND

The cutting of materials with the aid of cutting electrodes energized by a suitable power source is a known technique that is being successfully employed, e.g., in the field of electrosurgery. Typical electrosurgical devices apply a electrical potential difference or a voltage difference between a cutting electrode and a patient's grounded body (monopolar arrangement) or between a cutting electrode and a return electrode (bipolar arrangement) to deliver electrical energy to the area where tissue is to be cut. The voltage is applied either as a continuous train of high frequency pulses, typically in the RF range, or as direct current (DC).

The prior art provides a number of exemplary designs of bipolar electrosurgical electrodes. For example, U.S. Pat. No. 5,108,391 describes a bipolar treating apparatus with a first active electrode and a second return electrode having exposed distal ends to define a bipolar tip for electrosurgically treating tissue. U.S. Pat. No. 5,700,262 describes a bipolar electrode with fluid channels for performing neurosurgery. Additional information about bipolar electrosurgical devices and knives can be found, e.g., in U.S. Pat. Nos. 4,202,337 and 4,228,800 as well as numerous other open literature sources.

Depending on the conditions, the application of a voltage to a monopolar electrode or between the cutting and return electrodes of a bipolar electrode produces a number of physical phenomena. Most prior art devices take advantage of one of these phenomena to perform the cut. In particular, one class of devices uses a gas stream that is generated around the cutting electrode. For example, U.S. Pat. No. 5,217,457 describes an electrosurgical apparatus using a stream of gas that shrouds the electrode and an electrosurgical apparatus incorporating this electrode for cutting biological tissue. U.S. Pat. No. 5,088,997 also teaches the use of a stream of gas for electrosurgical procedures for coagulating or cutting biological tissue. On the other hand, U.S. Pat. No. 5,300,068 teaches an electrosurgical apparatus for cutting tissue and for ablating occlusions using arc discharges produced on a monopolar electrode in response to a train of pulses. Taking advantage of a yet different phenomenon, U.S. Pat. No. 6,352,535 teaches a method and device for electro microsurgery in a physiological liquid environment that uses high voltage electrical discharges of sub-microsecond duration in a liquid medium to produce cavitation bubbles. The cavitation bubbles have a size in the sub-millimeter range and are used for high-speed precision cutting with an inlaid disc electrode.

In addition to taking advantage of different phenomena to perform the cut, prior art devices employ various techniques for generating and applying the voltage to the electrode or electrodes. U.S. Pat. No. 6,135,998 teaches an electrosurgical device which uses extremely short monopolar voltage pulses, typically shorter than 200 ns, to drive an electrode having an inlaid disc geometry. This invention attempts to mitigate some of the negative cavitation effects, such as the damaging jets formed after the collapse of the cavitation bubble. U.S. Pat. No. 5,108,391 describes a high frequency generator for tissue cutting and for coagulating in high-frequency surgery. This device uses an electric arc discharge to perform the cutting operation. U.S. Pat. No. 6,267,757 teaches a device which uses radio-frequency (RF) ablation for revascularization. It employs a source, which delivers at least one burst of RF energy over an interval of about 1 to about 500 ms, and preferably about 30 to about 130 ms. This device has an elongated insulated, electrical conducting shaft with an uninsulated distal tip, which is configured to emit the RF energy. U.S. Pat. No. 6,364,877 also describes the use of high frequency pulses applied in a continuous manner. The teaching found in U.S. Pat. Nos. 5,697,090 and 5,766,153 suggests that a continuous train of high frequency pulses can be pulsed at a rate sufficient to allow the electrode to cool.

Unfortunately, despite all the above teachings, electrosurgical methods and apparatus generally suffer from an inability to control the depth of tissue damage (necrosis) in the tissue being treated. Most electrosurgical devices described above rely on a gas jet, an arc discharge or cavitation bubbles to cut, coagulate or ablate tissue. Such imprecise cutting methods cause tissue necrosis extending up to 1,700 µm into surrounding tissue in some cases.

In an effort to overcome at least some of the limitations of electrosurgery, laser apparatus have been developed for use in arthroscopic and other procedures. Lasers do not suffer from electrical shorting in conductive environments and certain types of lasers allow for very controlled cutting with limited depth of necrosis. U.S. Pat. No. 5,785,704 provides an example of a laser used for performing stereotactic laser surgery. Unfortunately, lasers suffer from limitations such as slow operating speed, inability to work in liquid environments, high cost, inconvenient delivery systems and other defects that prevent their more universal application. For these reasons, it would be desirable to provide improved apparatus and efficient methods for driving an electrosurgical apparatus for ablating tissue in a highly controlled and efficient manner while minimizing tissue damage.

The prior art has attempted to provide for more controlled electrosurgery by relying on plasma-mediated cutting and ablation of soft biological tissue in conductive liquid media at low temperatures. The fundamentals of this approach, which is used predominantly in the continuous pulse regime, and various embodiments employing it are described in the patents of Arthrocare including U.S. Pat. Nos. 5,683,366; 5,697,281; 5,843,019; 5,873,855; 6,032,674; 6,102,046; 6,149,620; 6,228,082; 6,254,600 and 6,355,032. The mechanism of low temperature ablation is called "coblation" and is described as electric field-induced molecular breakdown of target tissue through molecular dissociation. In other words, the tissue structure is volumetrically removed through molecular disintegration of complex organic molecules into non-viable atoms and molecules, such as hydrogen, oxides of carbon, hydrocarbons and nitrogen compounds. This molecular disintegration completely removes the tissue structure, as opposed to transforming the tissue material from solid form directly to a gas form, as is typically the case with ablation (see U.S. Pat. No. 5,683,366). More specifically, this mechanism of ablation is described as being associated with two factors: (1) "photoablation" by UV light at 306-315 nm and visible light at 588-590 nm produced by the plasma discharge; and (2) energetic electrons (e.g. 4 to 5 eV) can subsequently bombard a molecule and break its bonds, dissociating a molecule into free radicals, which then combine into final gaseous or liquid species (see U.S. Pat. No. 5,683,366). Surface temperature of tissue in this process is maintained between 40-70° C. This type of ablation mechanism has low rate of tissue dissection and a very limited applicability to hard tissues such as, for example, bones.

Despite these new advances the electrosurgical techniques are still experiencing a number of problems remain. First and foremost, the amount of power required to operate the prior art cutting devices remains in a high range of several Watts which precludes applications of these devices to such delicate organs as an eye. Second, the devices exhibit large energy and heat losses. These high losses translated into excessive power deposition into the tissue being ablated. Additional heat losses to the hand piece are also substantial. Third, even the best prior art devices operating at the lowest power levels have difficulties cutting hard biomaterials like bones and non-conducting materials such as cellulose or plastics.

Increasingly sophisticated surgical procedures create a growing demand for more precise and less traumatic surgical devices. The critical importance and delicate nature of the eye makes the demand for precision and safety of intraocular microsurgical instrumentation particularly important. For these and other reasons, it would be a major advance in the art to provide an apparatus and method for ablating materials at low power levels. It would be particularly useful to provide such apparatus and method that reduces heat losses to the material being cut as well as into the surroundings and, especially the hand piece. Furthermore, it would also be an advance to expand the range of materials that can be ablated to include biological tissue, cellulose and plastics.

OBJECTS AND ADVANTAGES

In view of the above shortcomings of the prior art, it is an object of the invention to produce a cutting apparatus and provide a method for operating it to achieve efficient thermal ablation at low power levels, e.g., ranging down to 10 mW, by overheating and evaporation in various types of materials including biological tissue. Specifically, it is an aim of the invention to minimize the damage zone produced during the cutting process by using plasma-assisted cutting and minimizing heat losses into the material being cut as well as the surroundings and the hand piece.

It is another object of the invention to provide a modulation format for pulsed operation of the cutting apparatus to minimize adverse effects in cutting biological tissue.

It is yet another object of the invention to reduce the voltage necessary for ionization of the gas to derive the plasma.

Yet another object of the invention is to provide a versatile cutting electrode geometry for efficient cutting and removal of material. Some of these electrodes and the driving waveforms are specifically designed for applications in eye surgery.

These and other objects and advantages will become apparent upon review of the following description and figures.

SUMMARY OF THE INVENTION

The objects and advantages of the invention are achieved by a method for cutting a material including conducting and non-conducting materials such as biological tissue, cellulose or plastic. During cutting the material is submerged in a conductive liquid medium. The method involves providing a cutting electrode with an elongate cutting portion and a return electrode. The elongate cutting portion has an aspect ratio of length to width larger than 1 and preferably larger than 5. A thin cutting electrode allows for dissection of tissue with low energy deposition. The two electrodes are immersed in the conductive medium and a voltage is applied between them such that the conductive liquid medium is heated to produce a vapor cavity around the elongate cutting portion and to ionize a gas inside the vapor cavity to produce a plasma. The presence of the plasma maintains electrical conductivity between the electrodes. The voltage applied between the electrodes is modulated in pulses having a modulation format selected to minimize the size of the vapor cavity, the rate of formation of the vapor cavity and heat diffusion into the material as the material is cut with an edge of the elongate cutting portion of the cutting electrode.

The modulation format includes pulses having a pulse duration in the range from 10 µs to 10 ms. Preferably, the pulses are composed of minipulses having a minipulse duration in the range between 0.1 and 10 µs and an interval ranging from 0.1 to 10 µs between the minipulses. Preferably, the minipulse duration is selected in the range substantially between 0.2 and 5 µs and the interval between them is shorter than a lifetime of the vapor cavity. The peak power of the minipulses can be varied from minipulse to minipulse.

When the method is used for cutting biological tissue it is preferable to use minipulses with alternating polarity. In other words, the modulation format contains minipulses that exhibit alternating positive and negative polarities. This modulation format limits the amount of charge transfer to the tissue and avoids various adverse tissue reactions such as muscle contractions and electroporation. In fact, additional devices for preventing charge transfer to the biological tissue can be employed in combination with this modulation format or separately when the method of invention is applied in performing electrosurgery.

In the same or in an alternative method of the invention the minipulses are further made up of micropulses. When the modulation format includes micropulses it is preferred that they have a duration ranging between 0.1 and 1 µs.

It is well-known that spark discharges develop in advance of an arc discharge. In accordance with the invention it is preferable to adjust the modulation format to permit spark discharges while preventing arc discharges. For example, the modulation format such as minipulse duration and peak power are adjusted to permit spark discharges while avoiding arc discharges. Furthermore, the voltage and the modulation format are selected such that the temperature of the elongate cutting portion of the cutting electrode and of the plasma are maintained significantly above the boiling temperature of water. Preferably, the temperature of the elongate cutting portion is maintained between about 100 and 1,000° C.

The invention further provides an apparatus for cutting materials submerged in the conductive liquid medium. The apparatus is equipped with the cutting electrode with the elongate cutting portion and return electrode. A voltage source is used for applying the voltage between the cutting and return electrodes to produce the vapor cavity with plasma. A pulse control is provided for controlling the modulation format of the voltage applied between the electrodes. The pulse control has a peak power control and a duration control for adjusting pulse power, pulse duration and pulse interval.

The shape of the cutting electrode and the elongate cutting portion can vary according to the material being cut. For a number of electrosurgical applications the elongate cutting portion should have a width between 1 µm and 200 µm and preferably between 10 µm and 100 µm. The elongate cutting portion can have various cross sections including circular, e.g., it is in the form of a wire. In these cases the entire cutting electrode can be in the form of a wire electrode. Application of a thin wire as a cutting electrode allows for reduction of power required for tissue dissection and reduces the depth of the damage zone produced at the edges of the cut. In order to perform certain types of cuts the elongate cutting portion can have one or more bends. For example, in certain electrosurgical applications the elongate cutting portion can be L-shaped or U-shaped. In some embodiments the elongate cutting portion can form a loop, e.g., it can be a looped wire electrode. In some embodiments it is advantageous to provide a device for advancing the wire electrode such that a length of the wire used for cutting can be adjusted during the application, when required. Such adjustment affects the impedance of the electrode and can be used for control of power dissipation. In addition, a fresh portion of the wire can be extended to replace the eroded portion. In one particular embodiment, the elongate cutting portion and the terminal portion of return electrode are both shaped into a shape suitable for capsulotomy.

In embodiments where transferring charge to the material should be avoided, e.g., when the material being cut is biological tissue, the apparatus has a device for preventing charge transfer to the non-conducting material. For example, a circuit with a separating capacitor, e.g., an RC-circuit, can be used for this purpose. The details of the invention are discussed below with reference to the attached drawing figures.

DETAILED DESCRIPTION

Figure 1:
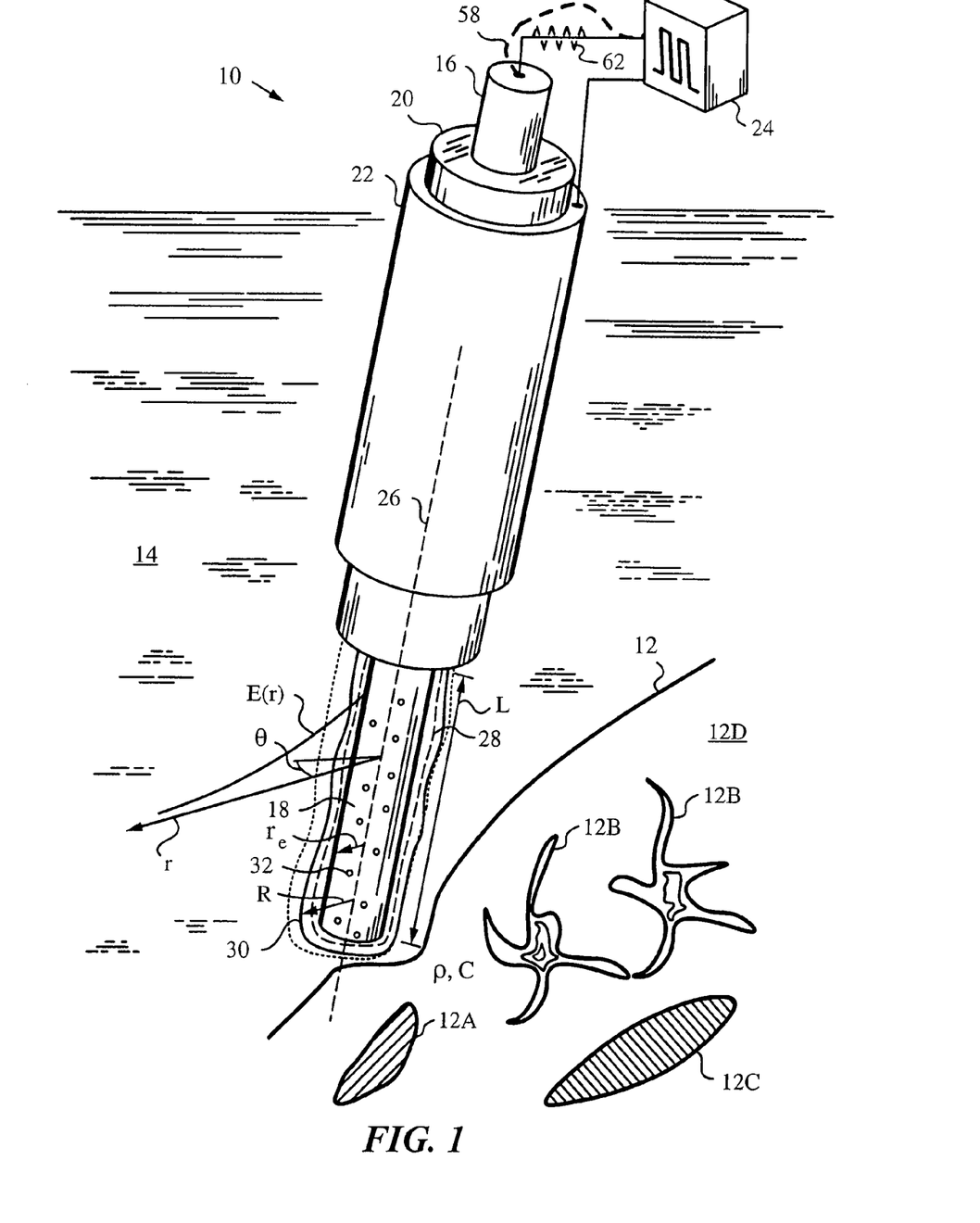
FIG. 1 shows a three-dimensional view of an apparatus according to the invention employed in cutting biological tissue.

FIG. 1 illustrates an apparatus 10 for cutting a material 12 submerged in a conducting liquid medium 14. In this embodiment material 12 is a biological tissue made up of various types of tissue including muscle tissue 12A, nerve tissue 12B, bone 12C and soft tissue 12D. In general, however, material 12 can be any conducting or non-conducting material which requires cutting and can include materials such as cellulose, e.g., wood and cellulose-based materials as well as various types of non-conducting plastics. Liquid medium 14 can be any type of electrolyte. In the present embodiment, liquid medium 14 is a physiological medium, for example an isotonic saline solution.

Apparatus 10 has a cutting electrode 16 with an elongate cutting portion 18. In the present embodiment, entire cutting electrode 16 is in the form of a wire electrode with circular cross section defined by a radius $r_e$. The material of wire electrode 16 can be any suitable conductor such as a metal like Tungsten, Titanium, Molybdenum, etc. or an alloy. In the present embodiment electrode 16 is made of Tungsten wire. Cutting electrode 16 is surrounded by an insulating layer 20 and a return electrode 22. Insulating layer 20 can be any dielectric material or combination of materials such as ceramic, plastic, glass, and/or air that provide electrical insulation between electrodes 16 and 22. Electrodes 16 and 22 are arranged coaxially along a center line 26. Cutting portion 18 protrudes beyond insulating layer 20 and return electrode 22. In fact, a length L of elongate cutting portion 18 is exposed. The aspect ratio of length L to width w ($w=2r_e$) of cutting portion 18 is at least 1 and preferably more than 5.

A voltage control unit 24 is connected to cutting electrode 16 and to return electrode 22. Voltage control unit 24 has a voltage generator for producing a voltage to be applied between electrodes 16, 22. Unit 24 also has a pulse control for pulsing the voltage in accordance with a predetermined modulation format, as described below. The pulse control has a peak power control and a duration control for adjusting a pulse power, a pulse duration τ and a pulse interval.

The operating principle of the method of invention is based upon formation of a thin layer of a plasma 28 around elongate cutting portion 18. To achieve this goal, electrodes 16, 22 of apparatus 10 are immersed in conductive medium 14 where tissue 12 is submerged and a voltage is applied between electrodes 16, 22 such that medium 14 is heated to produce a vapor cavity 30 around cutting portion 18. During heating an amount of medium 14 is vaporized to produce a gas 32 inside vapor cavity 30. In the present case medium 14 is saline and thus gas 32 is composed predominantly of water vapor, a small amount of oxygen and hydrogen and trace amounts of NaCl. The layer of gas 32 is ionized in the strong electric field around cutting electrode 16 to make up the thin layer of plasma 28. Because plasma 28 is electrically conductive it maintains electrical conductivity between electrodes 16, 22.

Figure 2:
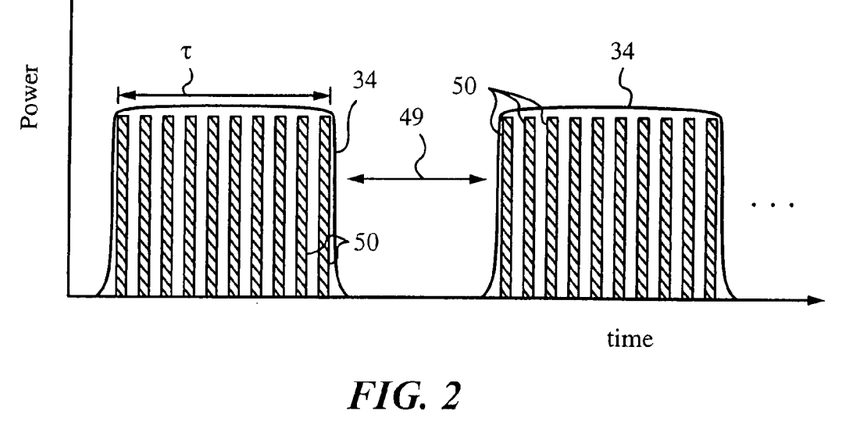
FIG. 2 is a graph illustrating a pulse modulation format according to the invention.

In contrast to the prior art, it is important that the size and rate of formation of vapor cavity 30 as well as heat diffusion into tissue 12 be minimized. The size and rate of formation of cavity 30 are related and can be minimized by modulating the voltage applied between electrodes 16, 22 by the pulse control of unit 24 in accordance with a modulation format. Specifically, pulse control modulates the applied voltage in pulses 34, as shown in FIG. 2. The modulation format of pulses 34 is selected to minimize the size of vapor cavity 30, the rate of formation of vapor cavity 30 and also heat diffusion into tissue 12.

Figure 3:
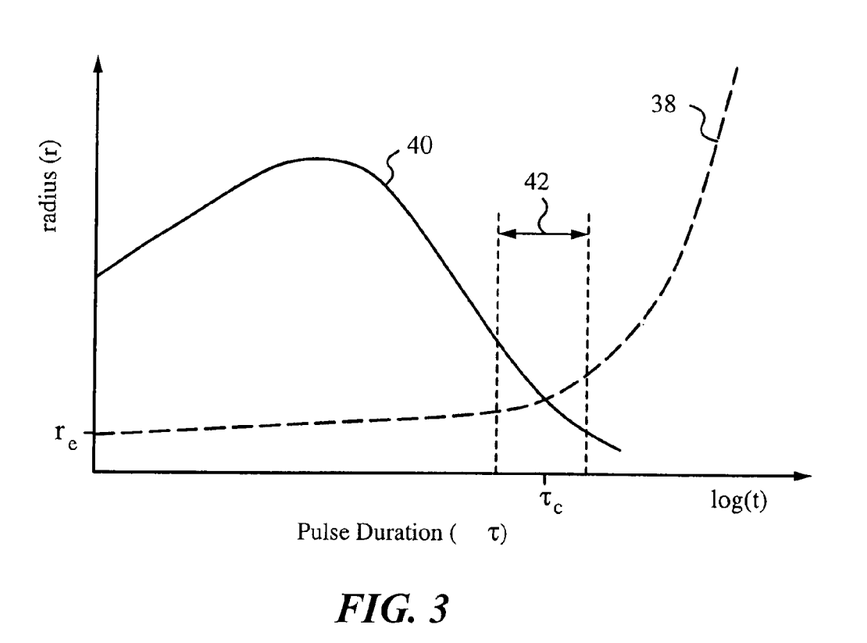
FIG. 3 is a graph indicating the qualitative dependence of the cavitation bubble diameter and heat diffusion on duration of the pulse.

To better understand the principles behind selecting the modulation format to achieve this minimization we now refer to the qualitative graphs in FIG. 3. Graph 38 illustrates the radius around elongate cutting portion 18 to which heat diffuses as a function of duration τ of pulse 34. As duration τ of pulse 34 increases heat diffuses deeper into tissue 12. This diffusion of heat causes thermal damage to tissue 12 and it is to be avoided. It should be noted, that the application of a long train of very high frequency pulses, e.g., RF pulses, will effectively act as one long pulse whose duration is equal to the entire duration of the pulse train. Hence, prior art devices operating in the continuous regime and applying RF pulses (see Background section) suffer from high heat diffusion and consequently cause large thermal damage to surrounding tissue.

Graph 40 illustrates the maximal radius of vapor cavity in this case also referred to as bubble 30 (see FIG. 1), or cavitation bubble, which is formed at constant pulse energy around cutting electrode 16. Now, the radius of cavitation bubble 30 initially increases with increasing pulse duration τ and then decreases and approaches zero as duration τ of pulse 34 tends to infinity (continuous current). Graphs 38 and 40 intersect at a pulse duration $τ_c$ at which heat diffusion is still relatively insignificant while the radius of bubble 30 is already small enough not to cause significant tissue damage. Thus, by choosing duration τ of pulse 34 in a range 42 around $τ_c$ heat damage and mechanical damage due to cavitation bubble 30 are minimized. In fact, choosing duration τ of pulses 34 so as not to produce large cavitation bubble 30 is equivalent to minimizing the size and rate of formation of vapor cavity 30. A person skilled in the art will appreciate that the exact shape of graphs 38, 40 and range 42 will vary depending on specific parameters such the exact composition of tissue 12, salinity of electrolyte 14 and geometry of electrode 16.

Figure 4A:
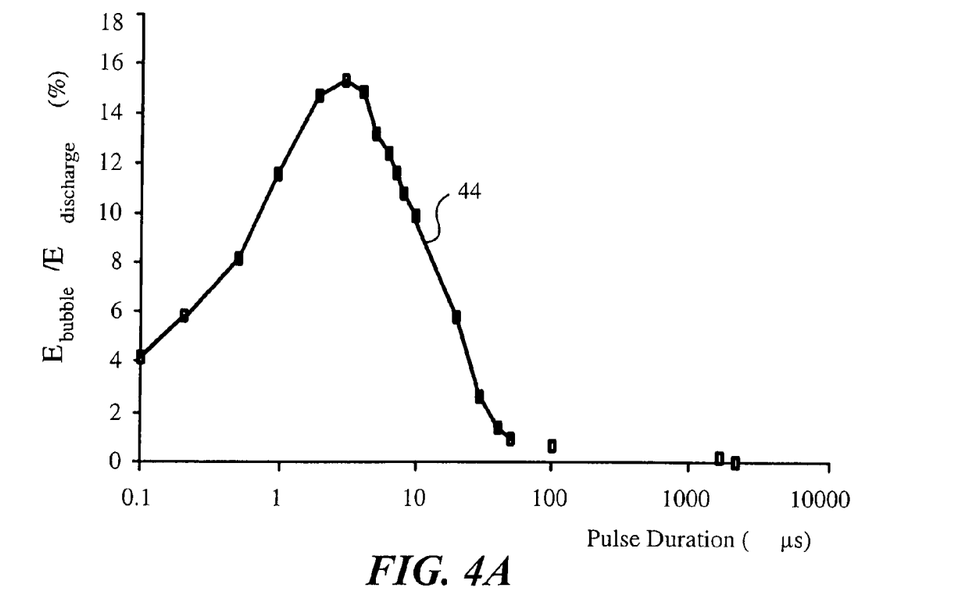
FIG. 4A is a graph illustrating the conversion of electrical energy of the discharge (1 mJ) into the mechanical energy of the bubble measured as a function of pulse duration for the apparatus of FIG. 1.
Figure 4B:
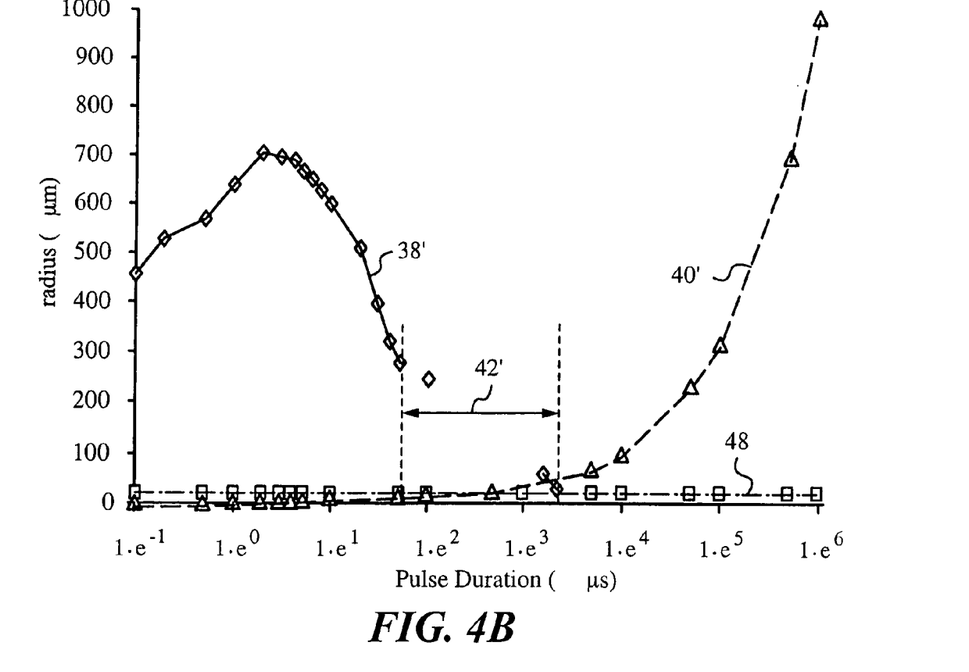
FIG. 4B is a graph illustrating the cavitation bubble size, energy deposition and heat diffusion as a function of pulse duration for the apparatus of FIG. 1.

FIG. 4A shows a graph 44 of the conversion of the electrical energy of the discharge for a discharge energy equal to 1 mJ and electrode 16 diameter of 25 μm into mechanical energy of bubble 30 measured as a function of duration τ of pulse 34. Efficiency of the conversion decreases with increasing duration τ of pulse 34 once pulse 34 is longer than about 3 μs. In FIG. 4B the radius of single bubble 30 is illustrated by graph 38' as a function of pulse duration τ in a 1 mJ discharge. At pulse duration τ above 50 μs a sequence of bubbles is formed with maximal radii reducing with increasing duration $τ_c$ as depicted by separate rhombuses. Graph 48 represents the penetration depth into material 12 of electric field E(r), here equal to radius $r_e$ of cutting portion 18. Graph 40' represents the radius around cutting portion 18 to which heat diffuses assuming constant temperature of cutting portion 18 in one dimensional geometry.

A range 42' in which pulse duration τ is optimized and in which both cavitation and heat diffusion are comparable with field penetration depth is between 50 μs and 2 ms. Under different conditions range 42' will vary, but optimal duration τ of pulses 34 will generally fall between 10 μs and 10 ms. In this range 42' the size and rate of formation of vapor cavity 30 as well as heat diffusion into tissue 12 are minimized. The thermal damage zone in tissue 12 due to heat diffusion is dependent mostly on duration τ of pulse 34. Specifically, varying duration τ of pulses 34 between 0.1 and 100 ms changes the depth of the heated zone in tissue 12 between 10 and 300 μm ranging from single cellular layer with no hemostatic effect to complete hemostasis in most of tissues 12A, 12B, 12C and 12D.

Referring back to FIG. 2, pulses 34 can be delivered in various modulation formats including continuous pulses or bursts of short pulses or minipulses 50. Preferably, pulses 34 are separated by a separation 49 of at least 1 ms, and preferably at least 10 ms while pulses 34 themselves are composed of a number of minipulses 50, as shown. The amplitude and duration of minipulses 50 determine the spatial extent and density of plasma 28. To avoid excessive overheating of tissue 12 the modulation format is adjusted so that plasma 28 is maintained at the regime of streamer and spark discharges but the arc discharges are prevented. Specifically, duration and peak power of minipulses 50 are adjusted to permit spark discharges and to prevent arc discharges. In most cases, limiting the duration of minipulses 50 to less than several μs will accomplish this goal. In fact, the duration of minipulses 50 should be kept in the range between 0.1 and 10 μs and preferably between 0.2 and 5 μs. The interval between minipulses 50 is preferably selected in the range between 0.1 and 10 μs. Such short times are sufficient for ionization and development of the spark discharges but not for creation of the arc discharge.

An arc discharge is a highly luminous and intensely hot discharge of electricity between two electrodes, in this case between electrode 16, and more precisely its cutting portion 18, and return electrode 22. The arc discharge is initiated when a strong electric forces draw electrons from one electrode to the other, initiating the arc. It is typically a continuous discharge characterized by high current and low voltage across the arc. On the other hand, a spark discharge has a high voltage and short duration.

If the intervals between minipulses 50 do not exceed a lifetime of vapor cavity 30 the ionization will be maintained by minipulses 50 until vapor cavity 30 collapses. Hence, in any situation, the intervals between minipulses 50 should be kept shorter than the lifetime of vapor cavity 30. For example, the lifetime of a 100 μm wide vapor cavity 30 is about 10 μs, thus minipulses 50 should be delivered at intervals not longer than 10 μs when working with such cavity width.

In contrast to prior art devices, apparatus 10 cuts tissue 12 using a side or edge of cutting portion 18, i.e., the entire length L of cutting portion 18 is available for performing the cut. Rapid and efficient ablation of tissue 12 is achieved when the temperature of cutting portion 18 and layer of plasma 28 around it are maintained significantly above the boiling temperature of water. In order to ensure that such temperature is efficiently maintained cutting portion 18 is long and thin, i.e., has a small radius—a few tens of microns—and an aspect ratio (length to width) of at least 1 and preferably at least 5. Such thin cutting portion 18 also reduces the amount of heat flow through the metal back into a hand piece (not shown).

In fact, heat flow W through cutting portion 18 is equal to:

$$W = χ \Delta T S/L,$$

where $S = πd^2/4$ is the cross section area of cutting portion 18. In the above equation χ is the coefficient of thermal conductivity and ΔT is the difference in temperature between the hot and cold parts of wire electrode 16, L is the length of cutting portion 18 and $d = 2r_e$. Evaporation rate of tissue 12 is equal to:

$$V = Ldv,$$

where v is the velocity of advance of cutting portion 18 through tissue 12. The amount of power deposited in tissue 12 to achieve such evaporation rate is:

$$P = V·ρ(C\Delta T_1 δ),$$

where $\rho$ is the density of tissue 12, C is its heat capacity, $\Delta T_1$ is the temperature rise from ambient to 100° C., and $\delta$ is the specific heat of evaporation (for tissue mostly composed of water the specific heat of evaporation of water $\delta=2.26\times10^3$ J/g can be used in the calculation). To prevent cooling of cutting portion 18 and of layer of plasma 28 by heat transfer via electrode 16, power deposition P should be kept significantly larger than the heat flow W, i.e., P>>W. In the present embodiment electrode 16 is made of Tungsten which has a heat conductivity $\chi=178$ W/m×K, $\Delta T_1=70°$ K and cutting portion 18 is advanced through tissue 12. For example, at $\Delta T=250°$ K and v=1 mm/s one obtains the condition $L^2/d>>14$ mm from the above equations. Therefore, to efficiently prevent cooling when cutting portion 18 has a length L=1 mm the diameter $d=2r_e$ of cutting portion 18 should be less than 70 μm. For $\Delta T=70°$ K and the rest of the parameters remaining the same we will obtain the conditions $L^2/d>>4$ mm. This means that a 1 mm long cutting portion 18 should not be thicker than 250 microns. The temperature of cutting portion 18 can be maintained as low as about 100° C., but it is preferably much higher, ranging up to 1000° C. In this temperature range tissue 12 is rapidly evaporated and thus ablated. Due to the turbulent flow of liquid boiling at the edges of vapor cavity 30 the interface with tissue 12 is only minimally overheated and damaged.

In the regime of heating produced by plasma 28 the temperature of cutting portion 18 is stabilized by a naturally occurring negative feedback mechanism as follows. In the areas where the vapor sheet of cavity 30 becomes thinner, the electric impedance is reduced and thus more current flows. The increased current results in increased generation of Joule heat in that area, and thus more electrolyte 14 is evaporated thereby increasing the thickness of vapor cavity 30 in that area. This mechanism stabilizes the thickness of vapor cavity 30 around cutting portion 18 and the thermal conditions of cutting portion 18. When tissue 12 is brought into ionized vapor cavity 30, thus reducing its thickness in that area, more current flows into tissue 12 than into plasma 28, since the impedance of tissue (which is typically similar to that of electrolyte 14) is much lower than that of plasma 28. Thus, more heat is generated in the area where tissue 12 is positioned inside vapor cavity 30.

Application of thin elongated electrode (for example a wire electrode) allows for minimization of the amount of material evaporated during tissue dissection as well as for minimization of the depth of the damage zone produced at the edges of the cut, as shown below. In the present embodiment, the electric field E(r) around cylindrical cutting portion 18 is reciprocal to the distance from it, and the density of Joule heat generated in liquid by the discharge is reciprocal to the square of that distance. Thus, thinner cutting portion 18 results in a more confined energy deposition. In fact, the electric field E(r) around cylindrical cutting portion 18 scales with distance r as follows:

$$E = \frac{E_e r_e}{r},$$

where $E_e$ is the value of the electric field on the surface of cutting potion 18. Thus, the difference in voltage on the surface of cutting portion 18 and at a distance R from electrode 16 is:

$$U_e - U_R = \int_R^{r_e} E(r)\,dr = E_e r_e (\ln R - \ln r_e).$$

The electric field becomes spherical at distances larger than length L of cutting portion 18, and thus it can be assumed that the electric potential drops to zero for distances larger than L. Therefore, the electric field $E_e$ at the surface of cutting portion 18 is:

$$E_e = \frac{U_e}{r_e(\ln L - \ln r_e)}.$$

The power density w of the Joule heat generated in electrolyte 14 is then:

$$w = j^2 \gamma = \frac{E_e^2}{\gamma} = \frac{U_e}{r_e(\ln L - \ln r_e)^2 \gamma},$$

where j is the current density and $\gamma$ is the resistivity of electrolyte 14. The minimal energy density for overheating of the surface layer of electrolyte 14 (assumed to be water) by pulse 34 of duration $\tau$ is:

$$A = w\cdot\tau = \rho\cdot C\cdot\Delta T,$$

where $\Delta T$ is the total temperature rise in the surface layer of electrolyte 14 during pulse 34, $\rho$ is the density of water and C is its heat capacity. Therefore, the voltage U required for initiation of vaporization during pulse 34 of duration $\tau$ is:

$$U = r_e(\ln L - \ln r_e)\sqrt{\rho\cdot C\cdot\Delta T\cdot\gamma/\tau}.$$

The voltage U and associated energy deposition can be reduced by decreasing the radius $r_e$ of cutting portion 18. In general, ambient temperature is about 30 CC when operating in biological tissue 12 of a live subject, boiling temperature is 100° C., $\rho=1$ g/cm$^3$, C=4.2 J/(g·K) and $\gamma\approx70$ Ohm·cm. With these values we obtain A≈300 J/cm$^3$ and U=260 V for pulse 34 of duration $\tau=0.1$ ms, $r_e=25$ μm and L=1 mm.

Since the electric field is reciprocal to the distance from the cylindrical electrode, the field efficiently penetrates into the electrolyte to the depth similar to the radius of the electrode. This minimal amount of energy required for creation of the vapor cavity around the electrode is:

$$A = w\cdot\tau = \rho\cdot C\cdot\Delta T\cdot\pi\cdot d^2\cdot L,$$

where d is the diameter of the electrode. Minimal depth of the damage zone at the edges of the cut will thus be similar to the radius of the electrode. Thus, reduction in radius of the electrode results in reduction in the power consumption and in the width of the damage zone produced at the edges of the cut. The threshold voltage $U_{th}$ required for reaching the threshold electric field $E_{th}$ to ionize gas 32 and produce plasma 28 is:

$$U_{th} = E_{th} r_e \ln(R/r_e),$$

where R is the radius of vapor cavity 30, as shown in FIG. 1. Threshold voltage $U_{th}$ can be decreased by reducing radius $r_e$ of cutting portion 18. This also results in a lower power dissipation and consequently in a smaller damage zone in tissue 12.

Vapor cavity 30 filled with plasma 28 and surrounding cutting portion 18 of cutting electrode 16 serves three major functions. First, it thermally isolates cutting electrode 16 from electrolyte 14 thus allowing for efficient heating. Second, the electric impedance of plasma 28 is much higher than that of tissue 12, thus Joule heating is generated mostly in plasma 28 and not in the surrounding liquid environment.

Third, since both electrical and thermal conductivity of tissue 12 is much higher than that of a vapor (gas 32), when tissue 12 is introduced inside vapor cavity 30 with plasma 28 it attracts both electric current and heat flow, which results in fast overheating and evaporation.

Another advantage of the cylindrical geometry of cutting electrode 16 as compared to prior art point sources (inlaid disc geometry) is that it allows for cutting tissue 12 with the side edge of cutting portion 18. Prior art point sources (see U.S. Pat. No. 6,135,998) produce a series of perforations when a train of pulses is applied. These perforations do not always form a continuous cut leaving behind bridges between the edges of the cut. To dissect these bridges the secondary scans are required and targeting these thin and often transparent straps of tissue is very difficult and time consuming. Cylindrical cutting portion 18 solves this problem by enabling the cutting by its edge and not only by its end or tip.

Figure 5:
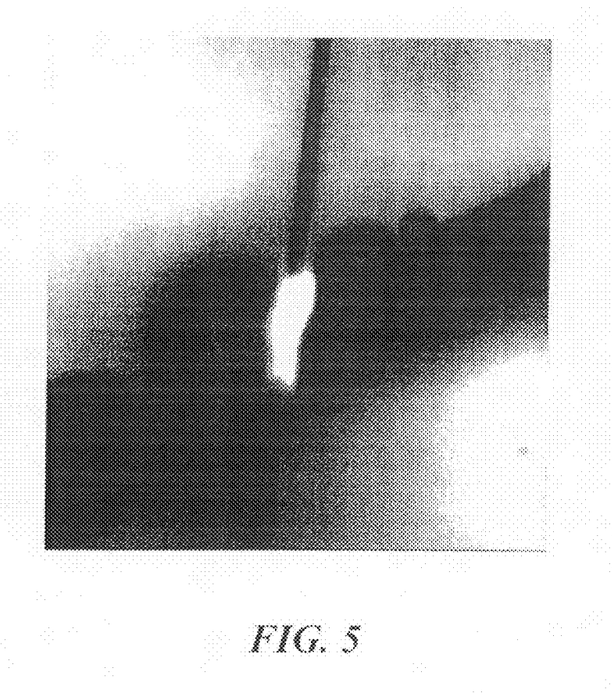
FIG. 5 is a photograph of the use of cutting electrode with elongate cutting portion for cutting paper.

In order to reduce unnecessary energy deposition, e.g., during electrosurgery, the voltage of source 24 can be set to a level which is sufficient for ionization of only a thin layer of vapor. Thus, in areas where vapor cavity 30 is too large (typically above several tens of microns) no plasma 28 will be formed. As a result, ionization and formation of plasma 28 will only take place in the areas of proximity or contact between generally conductive tissue 12 and conductive cutting portion 18. In other parts of vapor cavity 30 gas 32 will not be ionized and thus it will electrically insulate cutting electrode 18 preventing heat deposition into the surrounding environment. FIG. 5 illustrates cutting electrode 16 with cutting portion 18 of radius $r_e$=25 μm immersed in isotonic saline solution touching the edge of a material 52. This figure shows clearly the formation of plasma 28 at the point of contact with material 52. In this case material 52 is made of cellulose and is in fact a sheet of paper. Cutting portion 18 is touching an edge of paper 52 that is about 250 μm thick. As is clearly seen, plasma 28 is generated only in the area of contact between cutting electrode 18 and paper 52.

Figure 6:
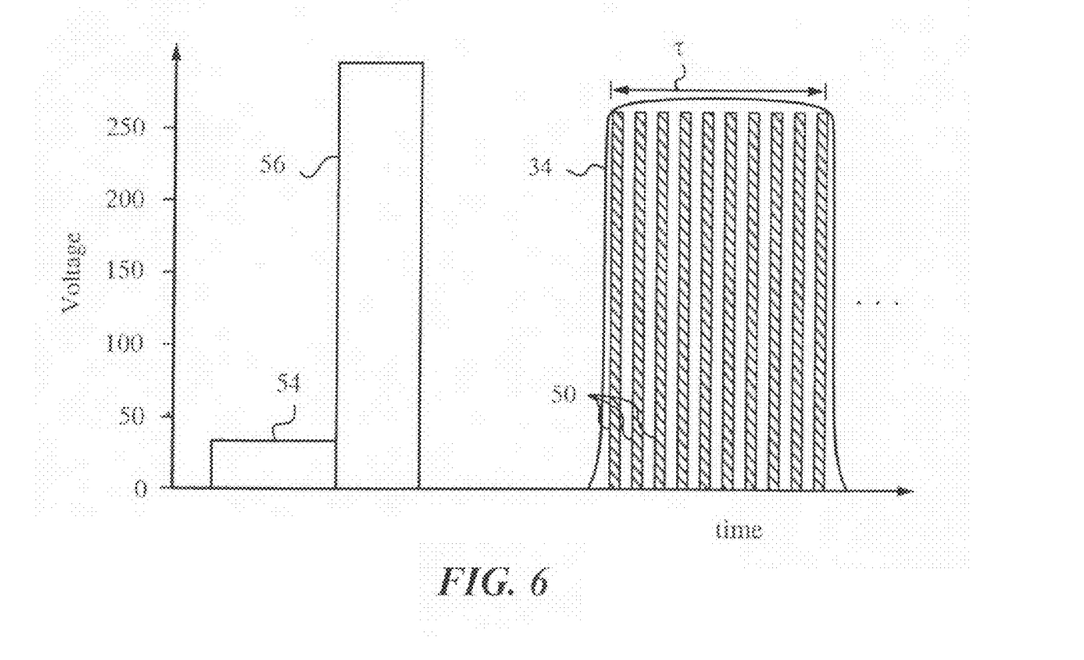
FIG. 6 is a graph of a pre-pulse and post-pulse used in accordance with the invention.

To further reduce the energy deposition cavity 30 can be created by electrochemical generation of gas 32, i.e., by electrolysis of water, rather than by its vaporization. For this purpose the pulse control and source 24 can vary the voltage between parts of the pulse or even between two successive pulses, as shown in FIG. 6. First, source 24 applies a pre-pulse 54 of relatively low voltage. This low voltage should be sufficient for electrolysis and can be in the range of several tens of Volts. In accordance with well-known principles, the application of such low voltage will yield oxygen gas on the anode and hydrogen gas on the cathode. The user can choose whether to use oxygen or hydrogen as gas 32 by selecting the polarity of pre-pulse 54, such that cutting portion 18 is either the anode or cathode. It should be noted, that applying a pulse composed of minipulses with alternating polarity (see FIG. 8 and below description) will generate a mixture of oxygen and hydrogen.

Next, pulse control and source 24 increase the voltage to a relatively high level in a post-pulse 56. The voltage of post pulse 56 can be in the range of several hundred Volts to complete the formation of vapor cavity 30 and to ionize gas 32 to form plasma 28. A sequence of combination pulses containing pre-pulse 54 and post-pulse 56 can be used to drive apparatus 10. Alternatively, a single combination pulse can be followed by a series of regular pulses 34 composed of minipulses 50, as described above. Embodiments of the method taking advantage of electrochemical generation of gas 32 around cutting portion 18 of electrode 16 obtain a substantial pulse energy reduction.

The rate of evaporation of electrolyte 14 depends on its temperature. There is always a delay between the moment when electrolyte 14 reaches boiling temperature (boiling temperature of water) and the moment when formation of vapor cavity 30 disconnects the current flowing through electrolyte 14 between electrodes 16, 22. When vapor cavity 30 forms, gas 32 stops the current flow and prevents further heating. Just before this time an additional energy is deposited that leads to overheating of electrolyte 14 and thus to explosive (accelerated) vaporization. This effect results in formation of a larger vapor cavity 30 and turbulence around cutting portion 18 of electrode 16. To prevent such overheating the energy for initial boiling should be delivered at a lower voltage, but as soon as vapor cavity 30 is formed, the voltage should be increased to achieve fast ionization of gas 32. Several solutions can be employed to address this problem.

In accordance with a first solution, a low impedance line 58, as indicated in dashed line in FIG. 1, is used instead of a standard electrical connection between the output of pulse generator in unit 24 and cutting electrode 16. In accordance to well-known principles, low impedance line 58 will cause the rising edge of a pulse to be reflected from the output end if the output impedance is high. This condition occurs when vapor cavity 30 is formed and not while electrode 16 is in direct contact with electrolyte 14. The reflection will oscillate within line 58 with a period determined by its length, and will form a high frequency (several MHz) modulation.

Figure 7:
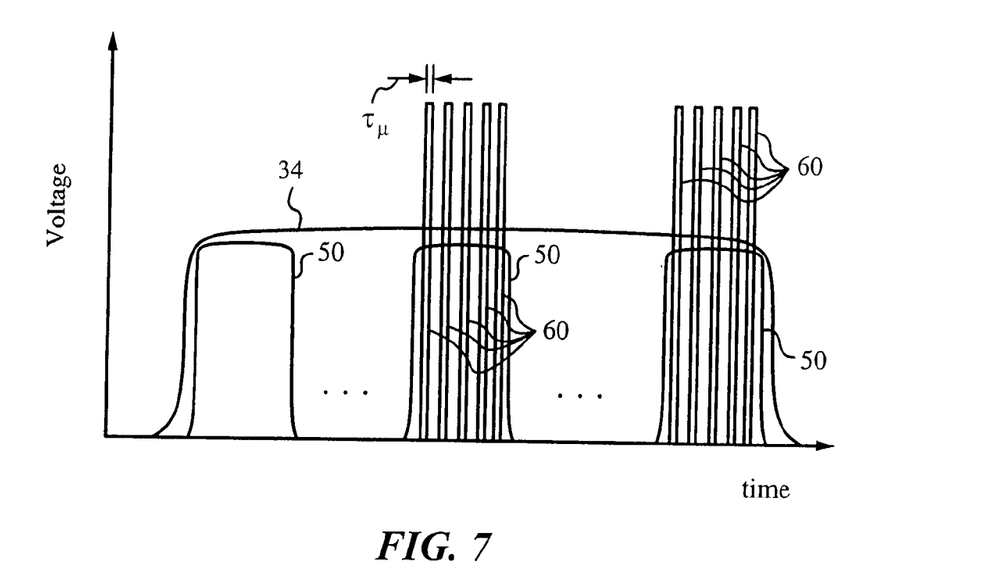
FIG. 7 is a graph illustrating the use of micropulses in accordance with the invention.

FIG. 7 illustrates the effect of line 58 on minipulses 50 in a pulse 34. The first set of minipulses 50 does not experience any changes because at this time the output impedance is still low (vapor cavity 30 not yet formed). Once vapor cavity 30 is formed reflection occurs and micropulses 60 are generated. As a result, each minipulse 50 gives rise to a series of micropulses 60. The length of line 58 is selected such that micropulses 60 have a duration $\tau_\mu$ the range between 0.1 and 1 μs. The voltage of micropulses 60 is twice as high as that of minipulse 50. This doubling in voltage of micropulses 60 is beneficial because it aids in ionizing gas 32 to form plasma 28 more rapidly and depositing more energy in plasma 28 than it was possible with minipulse 50 at the lower constant voltage level. That is because energy deposition increases as the square of the voltage and only linearly with the amount of time the voltage is applied. Hence, although micropulses 60 are applied at electrode 16 only about half the time of a minipulse 50, their doubled voltage raises the energy deposition by a factor of four.

In accordance with another solution an increase in the rate of ionization of gas 32 is achieved by adding a ballast resistor 62 in series with the load, as shown in dashed lines in FIG. 1. The resistance of resistor 62 ($R_{ballast}$) is selected to be higher than the impedance of the discharge in electrolyte 14 ($R_{electrolyte}$) but lower than in the ionized vapor or gas 32. As a result, the heating of electrolyte 14 before evaporation will proceed at a lower voltage $U_{low}$:

$$U_{low} = U/(1 + R_{ballast}/R_{electrolyte}).$$

The reduced voltage will slow the boiling and cause formation of thinner vapor cavity 30. After evaporation the impedance will greatly increase, resulting in an increase of the discharge voltage to a high value $U_{high}$:

$$U_{high} = U/(1 + R_{ballast}/R_{vapor}).$$

At this high voltage ionization of gas 32 will proceed rapidly. Specifically, when cutting portion 18 has a diameter of 50 μm and its length L=1 mm the impedance of the discharge in saline 14 is about 500Ω, while in plasma 28 it is about 6 kΩ. Thus, for example, a ballast resistor of 1 kΩ will provide output voltages of $U_{low}=U/3$ and $U_{high}=U/1.17$, respectively. The lower limit to the voltage applied during the heating phase is set by how much the duration of minipulses 50 and pulses 34 can be increased without unacceptable thermal damage to tissue 12 is caused by increased heat diffusion.

Figure 8:
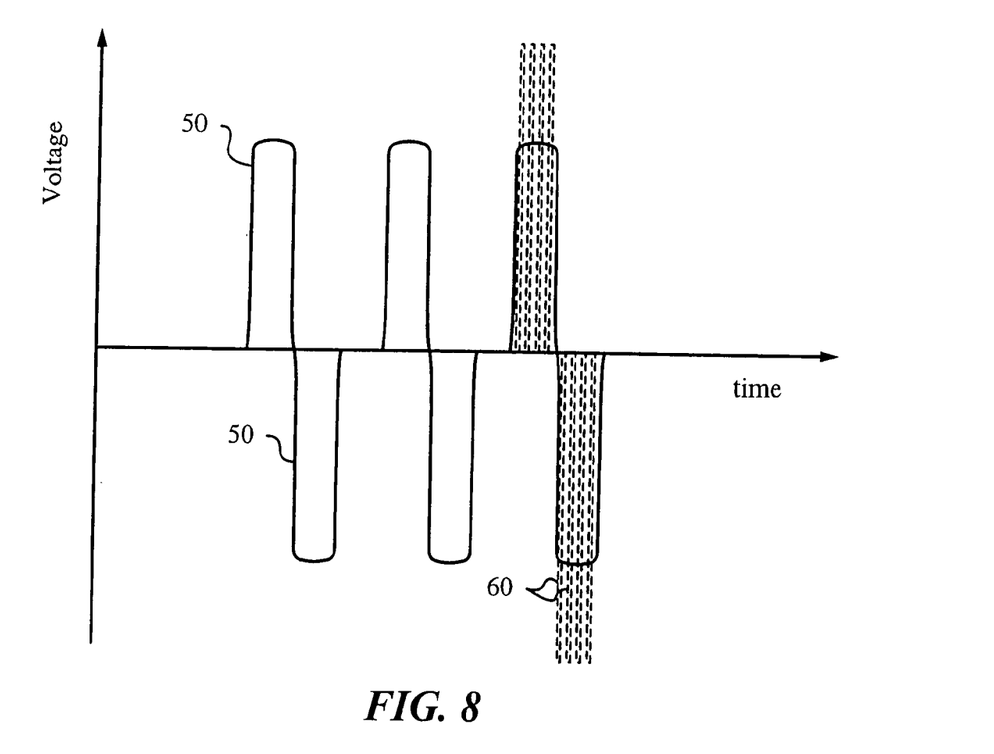
FIG. 8 is a graph illustrating the use of minipulses of alternating polarity in accordance with the invention.

In yet another embodiment the method of invention is adapted specifically for cutting biological tissue 12 containing muscle tissue 12A and nerve tissue 12B. It is known that electric excitation of nerve tissue 12B leads to contractions in muscle tissue 12A. In order to avoid contraction of muscle tissue 12A and reduce the risk of electroporation of adjacent tissue the method of invention calls for limiting and preferably stopping any charge transfer to tissue 12. This is achieved by using minipulses 50 of alternating positive and negative polarities, as illustrated in FIG. 8. Low impedance line 58 can also be used to generate micropulses 60 when vapor cavity 30 is formed.

The polarities are set by the voltage source of unit 24 in accordance with well-known electronics techniques. In the present embodiment the alternating polarities can be produced by a separating capacitor (not shown). The discharge time constant of the RC circuit, where R is the resistance of the discharge, should not exceed the excitation time of nerve cells in nerve tissue 12B at the applied voltage level. A person skilled in the art will appreciate that exact RC time constant will have to be adjusted on a case-by-case basis. In general, however, contractions of muscle tissue 12A will be prevented at a voltage level of 500 Volts if the discharge time does not exceed 1 μs. When cutting portion 18 has a diameter of 50 μm and length L=1 mm the electrical impedance is about 500Ω, and hence the capacitance of capacitor should not exceed 2 nF. It should be noted that in addition to preventing muscular contractions, alternating polarity of minipulses 50 reduces the effect of electroporation, as compared to direct current (DC) (only positive or only negative voltage) pulses.

Figure 9:
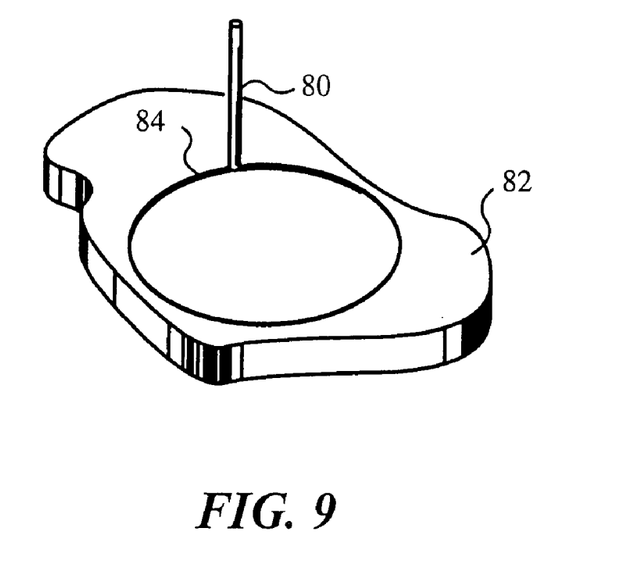
FIG. 9 illustrates an apparatus of the invention used in cutting a material.

Various alternatives can be introduced to the apparatus of invention depending on the material being cut and the type of cut required. For example, in FIG. 9 a cutting electrode 80 of an apparatus analogous to apparatus 10 is used for performing a circular incision 84 in a material 82. The return electrode and liquid conducting medium are not shown in this drawing. Material 82 is a thin sheet of plastic or biological material. When used for performing biopsy, a cylindrical biopsy can be easily obtained in this manner without bleeding.

Figure 10:
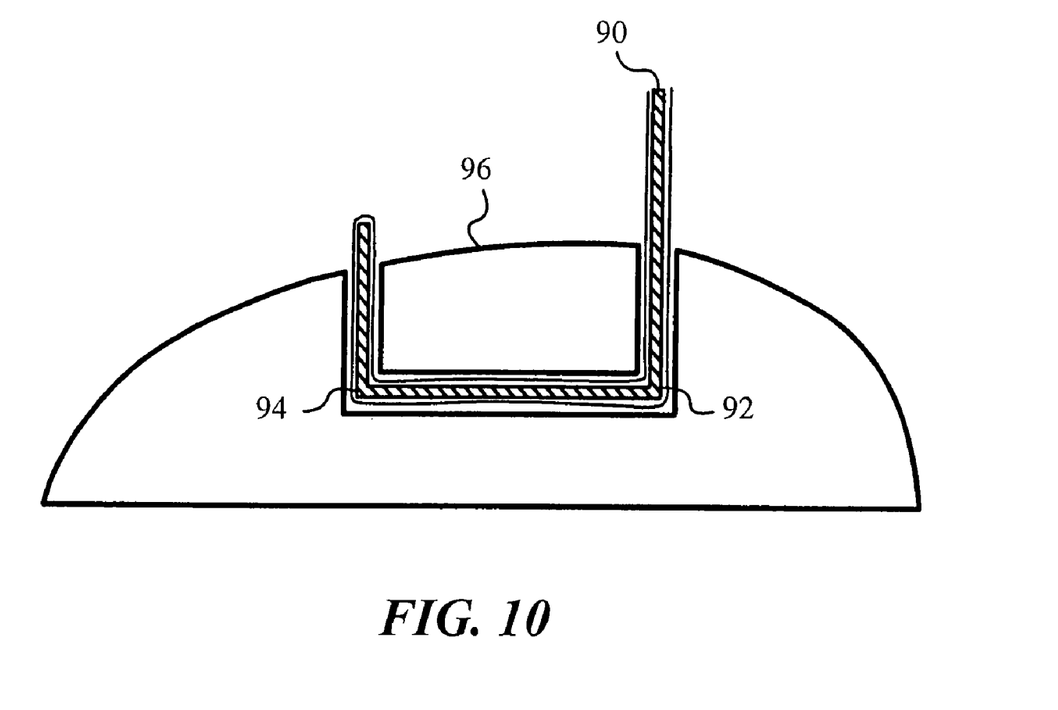
FIG. 10 illustrates an apparatus of the invention using a shaped cutting electrode.

FIG. 10 illustrates a cutting electrode 90 having two bends 92, 94 to form a U-shaped electrode. The return electrode and liquid conducting medium are not shown in this drawing. Cutting electrode 90 is used for removing a large amount of a material 96 with a single cut. U-shaped cutting electrode 90 can be used to minimize the damage to tissue in electrosurgery and to maximize the lifetime of cutting electrode 90. In an alternative version a cutting electrode with a single bend can be used to make and L-shaped cutting electrode. In general, bends at various angles can be introduced to cutting electrode to perform any desired type of cut, to approach tissue at various angles and to manipulate the tissue before and during the cutting.

Figure 11A:
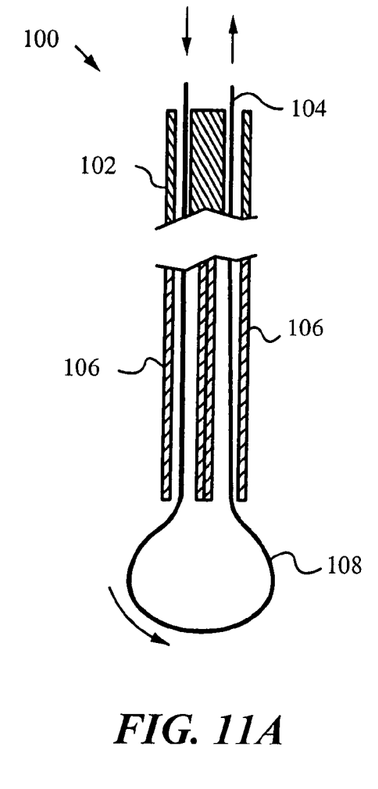
FIGS. 11A-C are partial views of alternative embodiments in accordance with the invention.

FIG. 11A illustrates a portion of yet another apparatus 100 having a mechanism 102 for advancing a cutting electrode 104. In this embodiment cutting electrode 104 is a wire electrode. Return electrode 106 is in the form of two capillaries through which wire electrode 104 is threaded. Capillaries 106 can be used for delivering an electrolyte and/or aspiring fluids during electrosurgery, i.e., capillaries 106 can be used for irrigation and suction. Cutting electrode 104 forms a loop 108 for cutting tissue in accordance with the method of the invention. Mechanism 102 allows the user to refresh cutting electrode as needed during operation. Exposure time of wire electrode 104 outside capillaries 106 should be smaller than its erosion lifetime. It should be noted that mechanism 102 can be used in other embodiments for both advancing and retracting the cutting electrode as necessary to maximize its lifetime and/or retract an eroded electrode.

Figure 11B:
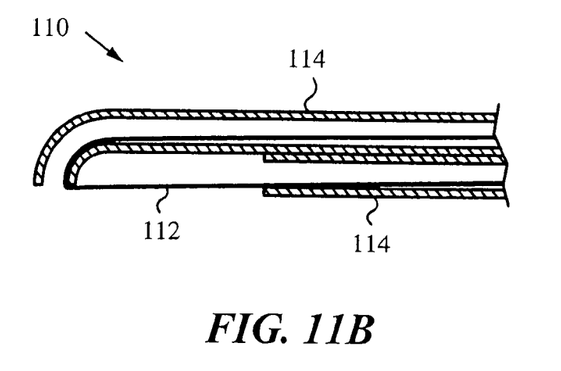
Figure 11C:
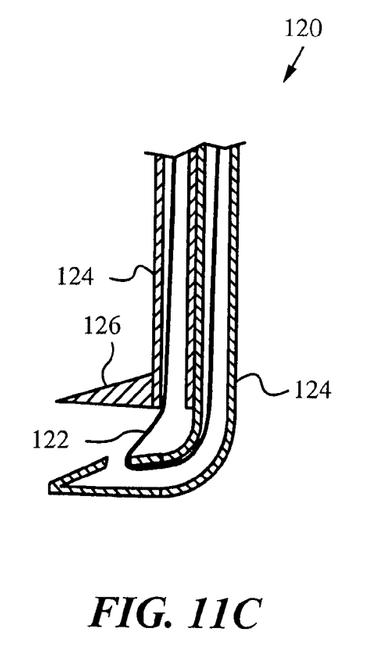

FIG. 11B illustrates a portion of an apparatus 110 using a wire electrode 112 threaded through capillaries 114. Capillaries 114 serve the dual function of return electrode and channels for delivering and aspiring fluids during operation. Apparatus 110 can be used as a frame saw, as required in electrosurgical applications. FIG. 11C illustrates a portion of still another apparatus 120 functioning as a stationary scissors for both lifting and cutting of tissue. Apparatus 120 has a cutting electrode 122 in the form of a wire threaded through two capillaries 124 functioning as the return electrode. Mechanism 102 allows the user to refresh cutting electrode as needed during operation. Exposure time of wire electrode 112 outside capillaries 114 should be smaller than its erosion lifetime. A projection 126 is used for lifting of tissue. Both apparatus 110 and apparatus 120 are operated in accordance with the method of the invention.

Figure 12:
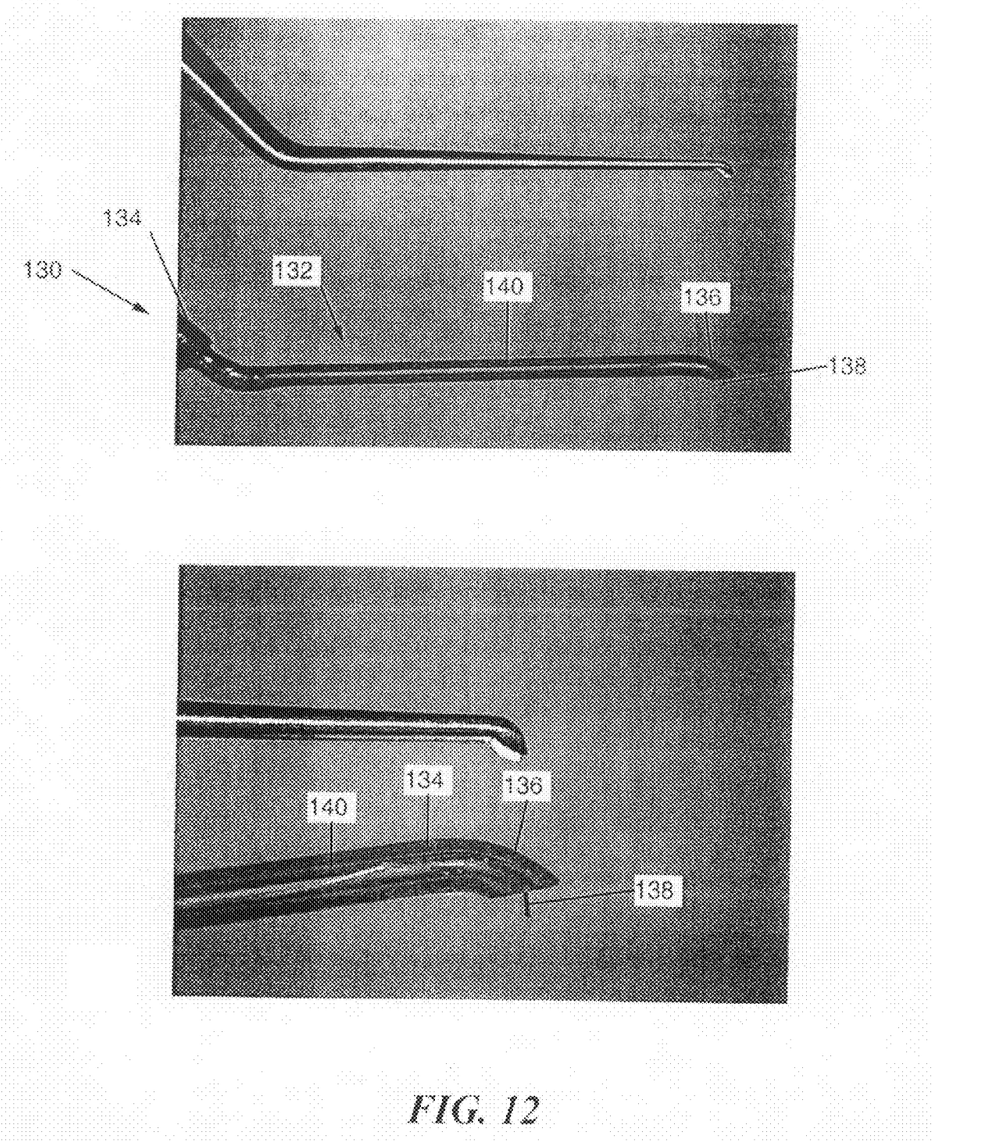
FIG. 12 illustrates an apparatus of the invention designed for capsulotomy.

FIG. 12 illustrates a portion of an apparatus 130 specifically designed for capsulotomy. An electrosurgical probe 132 for capsulotomy has a shape similar to the mechanical tools used for capsulotomy in order to make its application easy and convenient for surgeons who are used to such mechanical tools (comparison is shown in the top photograph). Probe 132 has an insulator 134 with external diameter varying between 0.1 and 1 mm, which has a bent tip 136 at the end. A cutting electrode 138 with a diameter varying between 10 to 200 microns protrudes from insulator 134 by a distance varying between 20 microns to 1 mm. A return electrode 140 can be either a concentric needle or an external electrode attached to the eye or somewhere else to the body of the patient. Apparatus 130 protects the tissue located above the lens capsule (cornea and iris) (not shown) from accidental contact with cutting electrode 138 thus ensuring its safe use during capsulotomy.

The apparatus and method of the invention ensure efficient thermal ablation at low power levels, e.g., ranging down to 10 mW by overheating and evaporation. Devices built in accordance with the invention can be used for cutting various types of materials including biological tissue while minimizing the damage zone and minimizing heat losses into the material being cut as well as the surroundings and the hand piece. The voltages necessary for producing the plasma are reduced significantly in comparison to prior art devices. Because of such power efficiency and low thermal damage the apparatus of invention and method for operating it can be adapted to numerous applications in surgery on very sensitive organs, such as the eye. For example, the apparatus of invention can be used for: (a) dissection of membranes and cutting retina in vitreoretinal surgery, (b) capsulotomy, (c) lensectomy, (d) iridectomy, (e) trabeculectomy.

A person skilled in the art will recognize that many extensions and alternative embodiments of the invention are possible and that the full breadth of the invention is hence defined by the scope of the appended claims and their legal equivalents.

We claim:

1. A system for plasma-mediated thermo-electrical surgery comprising:
a cutting electrode having an elongate cutting portion having a length greater than its width, wherein the width is less than 250 μm;

a return electrode adapted to attach to the body of a patient remote from the cutting electrode; and a voltage control unit coupled to the cutting electrode and configured to provide a plurality of voltage pulses to the cutting electrode, wherein the voltage control unit comprises:

a voltage source and a pulse control configured to control the voltage applied to the cutting electrode from the voltage source, so that the voltage applied comprises a plurality of pulses each separated by an interval greater than 1 ms, wherein the duration of each pulse is between about 2 µs and 200 µs, and each pulse comprises a plurality of minipulses.

2. The system of claim 1, wherein the voltage control unit is further configured so that the minipulses are of alternating positive and negative polarities.

3. The system of claim 1, wherein the voltage control unit is further configured to vary a peak power of the minipulses.

4. The system of claim 1, wherein the voltage control unit is further configured so the duration of each minipulse is less than about 5 µsec.

5. The system of claim 1, further comprising a charge transfer prevention device coupled to the voltage control unit.

6. The system of claim 5, wherein the charge transfer prevention device comprises a capacitor.

7. The system of claim 1, further comprising a low impedance line electrically connecting the voltage control unit to the cutting electrode, whereby the low impedance line reflects the pulses.

8. The system of claim 1, further comprising a ballast resistor electrically connected between the cutting electrode and the voltage control unit.

9. The system of claim 1, wherein the elongate cutting portion has a width between about 1 µm and about 100 µm.

10. The system of claim 1, wherein the elongate cutting portion is circular in cross section.

11. The system of claim 1, wherein the elongate cutting portion defines at least one bend.

12. The system of claim 1, wherein the elongate cutting portion defines a loop.

13. The system of claim 1, wherein the cutting electrode comprises a wire electrode.

14. The system of claim 1, wherein the elongate cutting portion has a diameter between about 10 microns and about 200 microns and extends from an adjacent insulator by about 20 microns to about 1 mm, and wherein the insulator has a diameter between about 0.1 mm and about 1 mm, and wherein the elongate cutting portion has a bent tip.

15. The system of claim 1, wherein a ratio of the length to width of the cutting portion is larger than five.

16. The system of claim 1, wherein the pulse control comprises a peak power control and a duration control configured to adjust the duration of the pulses and the pulse interval.

17. The system of claim 1, wherein the duration of each pulse is about 0.1 ms.

18. A system for plasma-mediated thermo-electrical surgery comprising:

a cutting electrode having an elongate cutting portion having a length greater than its width, wherein the width is less than 250 µm;

a return electrode adapted to attach to the body of a patient remote from the cutting electrode; and a voltage control unit coupled to the cutting electrode and configured to provide the cutting electrode with a plurality of pulses each separated by an interval of greater than 1 ms, and each of the pulses comprises a plurality of minipulses; wherein the voltage control unit comprises a voltage source, and a pulse control having a duration control configured to adjust the duration of the pulses between about 2 µs and 200 µs, and further configured to adjust the interval between the minipulses.

19. A system for plasma-mediated thermo-electrical surgery comprising:

a cutting electrode having an elongate cutting portion having a length at least five times greater than its width, wherein the width is less than 100 µm;

a return electrode adapted to attach to the body of a patient remote from the cutting electrode; and a voltage control unit coupled to the cutting electrode and configured to provide a plurality of pulses each separated by an interval greater than 1 ms, wherein the duration of each pulse is between about 2 µs and 200 µs, and each pulse comprises a plurality of minipulses each separated by an interval; wherein the voltage control unit comprises:

a voltage source, and a pulse control configured to produce vaporization and ionization at the cutting portion during each pulse, and to terminate plasma discharge between the pulses.

\* \* \* \* \*